United States Patent [19]

Kaplan

[11] Patent Number: 4,521,619

[45] Date of Patent: Jun. 4, 1985

[54] THERAPEUTICALLY USEFUL SULPHUR-CONTAINING BENZYLIDENE DERIVATIVES

[75] Inventor: Jean-Pierre Kaplan, Bourg la Reine, France

[73] Assignee: Synthelabo, Paris, France

[21] Appl. No.: 552,901

[22] Filed: Nov. 17, 1983

[30] Foreign Application Priority Data

Nov. 29, 1982 [FR] France ............................... 82 19982

[51] Int. Cl.³ .................. C07C 143/80; C07C 143/64; A61K 31/40; C07D 211/54
[52] U.S. Cl. .......................... 514/315; 260/509; 546/229; 548/542; 514/424; 514/603; 564/89; 424/268
[58] Field of Search ................. 564/89; 548/542; 546/229; 260/509

[56] References Cited

U.S. PATENT DOCUMENTS 2,120,512 6/1938 Rosenhauer ..................... 564/89
4,098,900 7/1978 Dittrich et al. .................. 564/89

Primary Examiner—Charles F. Warren
Assistant Examiner—R. A. Picard
Attorney, Agent, or Firm—Wegner & Bretschneider

[57] ABSTRACT

Benzylidene derivatives of the formula:

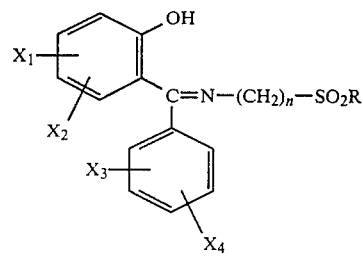

wherein n represents an integer from 1 through 4, R represents an amino radical, a monoalkylamino group containing 1 through 4 carbon atoms in the alkyl radical, a dialkylamino group containing 1 through 4 carbon atoms in each alkyl radical, or when n represents 2, 3 or 4 a group

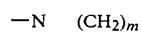

in which m represents 4 or 5, or a group —OM in which M represents an alkali metal or alkaline earth metal, and $X_1$, $X_2$, $X_3$ and $X_4$ each represent a hydrogen atom, a halogen atom, or an alkyl radical containing 1 through 6 carbon atoms, are new therapeutically useful compounds. They possess antidepressant, anticonvulsant, anxiolytic, analgesic, anti-inflammatory, ulcer-inhibiting, gastric antisecretory and antihypertensive properties.

7 Claims, No Drawings

THERAPEUTICALLY USEFUL SULPHUR-CONTAINING BENZYLIDENE DERIVATIVES

The present invention relates to new therapeutically useful sulphur-containing benzylidene derivatives, to a process for their preparation and their application in therapy such as pharmaceutical compositions containing them.

The sulphur-containing benzylidene derivatives of the present invention are those compounds of the general formula:

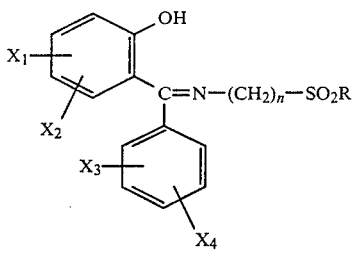
(I)

wherein n represents an integer from 1 to 4, R represents an amino radical (—$NH_2$), a monoalkylamino group containing 1 to 4 carbon atoms in the alkyl radical, a dialkylamino group containing 1 to 4 carbon atoms in each alkyl radical, or when n represents 2, 3 or 4 a group

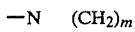

in which m represents 4 or 5, or a group —OM in which M represents an alkali metal, e.g. sodium, or alkaline earth metal, e.g. calcium or magnesium, and $X_1$, $X_2$, $X_3$ and $X_4$ each represent, independently of one another, a hydrogen atom, a halogen atom, or a straight- or branched-chain alkyl radical containing 1 to 6 carbon atoms.

The preferred compounds of the invention are those of the general formula:

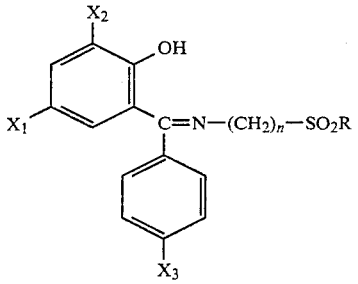
(II)

(wherein the various symbols are as hereinbefore defined), and more particularly those such compounds in which n represents 2 or 3, R represents the amino radical or a diethylamino group, or a group —ONa, —O-Ca/2 or —OMg/2, $X_1$ represents a halogen atom (preferably chlorine) or the methyl radical, $X_2$ represents a hydrogen atom or a straight- or branched-chain alkyl radical containing 1 to 6 carbon atoms, and $X_3$ represents a halogen atom (preferably chlorine) or the methyl radical. Of outstanding importance are 3-[5-chloro-2-hydroxy-3-methylphenyl)(4-chlorophenyl)methylene]-aminopropanesulphonamide and 2-[(5-chloro-2-hydroxy-3-methylphenyl)(4-chlorophenyl)methylene]-aminoethanesulphonamide.

According to a feature of the present invention, the sulphur-containing benzylidene derivatives of general formula I are prepared by the process which comprises reacting a benzophenone of the general formula:

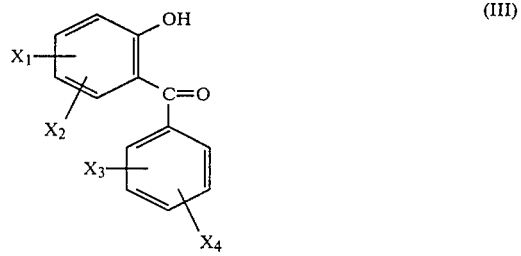
(III)

(wherein the various symbols are as hereinbefore defined) with a compound of the general formula:

$$H_2N—(CH_2)_n—SO_2R \qquad (IV)$$

(wherein n and R are as hereinbefore defined), optionally in the form of an acid addition salt such as the hydrochloride, at a temperature of 20° to 120° C. in an organic solvent medium, such as methanol, ethanol or a methanol/toluene mixture, in the presence of a base, for example an alkali metal alkoxide such as sodium methoxide or ethoxide.

The compounds of general formula I wherein R represents a group —OM (M being as hereinbefore defined) can be obtained from corresponding compounds wherein R represents the hydroxy radical by methods known per se, viz. methods heretofore used or described in the chemical literature for preparing alkali metal or alkaline earth metal salts of sulphonic acids.

The benzophenone starting materials of general formula (III) can be prepared by application of the method described in French Pat. No. 81/21559 or corresponding British Patent Application No. 8232766 (published under Serial No. 2111051A).

The Examples which follow illustrate the preparation of the sulphur-containing benzylidene derivatives of the present invention by the hereinbefore described process. The analyses and the IR and NMR spectra confirm the structures of the compounds obtained.

EXAMPLE 1

3-[(5-Chloro-2-hydroxy-3-methylphenyl)(4-chlorophenyl)methylene]-aminopropanesulphonamide

[$X_1$=5-Cl, $X_2$=3-$CH_3$, $X_3$=4-Cl, $X_4$=H, n=3, R=$NH_2$]

A mixture of 7 g (0.0249 mol) of (5-chloro-2-hydroxy-3-methylphenyl)(4-chlorophenyl)-methanone with 4.35 g (0.0249 mol) of 3-aminopropanesulphonamide hydrochloride and 1.38 g (0.0255 mol) of sodium methoxide in 750 ml of methanol is heated under reflux for 10 hours, with stirring. It is then evaporated to dryness under reduced pressure. The residue is treated with 350 ml of methylene chloride and 150 ml of water. The organic phase is decanted, dried over $MgSO_4$ and filtered and the filtrate is evaporated to dryness. The residue obtained crystallises on trituration in 100 ml of petroleum ether. The precipitate is filtered off on a frit and washed with 50 ml of petroleum ether. It is then recrystallised from 25 ml of ethyl acetate; during the recrystallisation, it is treated whilst hot for 5 minutes with 0.5 g of vegetable charcoal. The crystals are filtered off, washed with 25 ml of diethyl ether, drained and dried in a heated desiccator at 60° C.

Melting point = 153°–154° C.

EXAMPLE 2

2-[(5-Chloro-2-hydroxy-3-methylphenyl)(4-chlorophenyl)methylene]-aminoethanesulphonamide

[$X_1$=5-Cl, $X_2$=3-$CH_3$, $X_3$=4-Cl, $X_4$=H, n=2, R=$NH_2$]

A mixture of 3.65 g (0.0284 mol) of taurinamide hydrochloride, 1.6 g (0.0289 mol) of sodium methoxide and 8 g of (5-chloro-2-hydroxy-3-methylphenyl)(4-chlorophenyl)-methanone in 600 ml of methanol and 200 ml of ethanol is heated at the reflux temperature for 10 hours. It is then evaporated to dryness. The residue is taken up in 600 ml of methylene chloride and the organic phase is washed with water, decanted, dried over $MgSO_4$ and filtered on a frit. The filtrate is evaporated to dryness. The product precipitates and is carried onto a frit with petroleum ether. It is drained and dried in a desiccator.

Melting point = 185°–186° C.

The following Table shows the compounds of the invention which have been prepared by way of examples.

TABLE

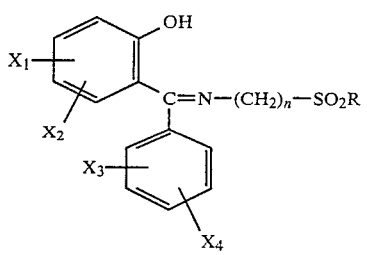

| Compound | n | $X_1$ | $X_2$ | $X_3$ | $X_4$ | R | M.p. (°C.) |
|---|---|---|---|---|---|---|---|
| 1 | 3 | H | H | H | H | ONa | >260 (dec) |
| 2 | 2 | H | H | H | H | ONa | 250 (dec) |
| 3 | 2 | 5-Cl | H | H | H | ONa | 260 (dec) |
| 4 | 2 | 5-F | H | H | H | $NH_2$ | 135 |
| 5 | 3 | 5-F | H | H | H | $NH_2$ | 108 |
| 6 | 2 | 5-Cl | H | 2-Br | H | ONa | 238 (dec) |
| 7 | 3 | 5-Cl | 3-$CH_3$ | 4-Cl | H | $NH_2$ | 153–154 |
| 8 | 2 | 5-Cl | 3-$CH_3$ | 4-Cl | H | $NH_2$ | 185–186 |
| 9 | 3 | 5-Cl | 3-$nC_6H_{13}$ | 4-Cl | H | ONa | 157–160 |
| 10 | 3 | 5-Cl | 3-$CH_3$ | 4-Cl | H | ONa | >250 |
| 11 | 3 | 5-Cl | 3-$CH_3$ | 4-Cl | H | OCa/2 | >250 |
| 12 | 3 | 5-Cl | 3-$nC_6H_{13}$ | 4-$CH_3$ | H | ONa | 125–130 |
| 13 | 3 | 5-Cl | 3-$nC_6H_{13}$ | 4-Cl | H | $NH_2$ | 94.5–95 |
| 14 | 3 | 5-Cl | 3-$nC_6H_{13}$ | 4-$CH_3$ | H | $NH_2$ | 101–101.5 |
| 15 | 2 | 5-Cl | 3-$CH_3$ | 4-Cl | H | OMg/2 | >250 |
| 16 | 2 | 5-Cl | 3-$CH_3$ | 4-Cl | H | ONa | >250 |
| 17 | 2 | 5-Cl | 3-$CH_3$ | 4-Cl | H | OCa/2 | >290 |
| 18 | 2 | 5-Cl | 3-$nC_6H_{13}$ | 4-Cl | H | ONa | 115–118 |
| 19 | 2 | 5-Cl | 3-$nC_6H_{13}$ | 4-$CH_3$ | H | ONa | 132–135 |
| 20 | 2 | 5-Cl | 3-$nC_4H_9$ | 4-$CH_3$ | H | ONa | 170–185 |
| 21 | 2 | 5-Cl | 3-$nC_6H_{13}$ | 4-Cl | H | $NH_2$ | 68–69 |
| 22 | 2 | 5-Cl | 3-$nC_4H_9$ | 4-Cl | H | ONa | 197–204 |
| 23 | 3 | 5-Cl | 3-$nC_3H_7$ | 4-$CH_3$ | H | $NH_2$ | 95–96 |
| 24 | 1 | 5-Cl | 3-$CH_3$ | 4-Cl | H | ONa | 218–220 |
| 25 | 3 | 5-Cl | 3-$nC_3H_7$ | 4-Cl | H | $NH_2$ | 118–119 |
| 26 | 3 | 5-Cl | 3-$nC_4H_9$ | 4-$CH_3$ | H | ONa | 219–221 |
| 27 | 2 | 5-$CH_3$ | 3-$C_2H_5$ | 4-$CH_3$ | H | $NH_2$ | 138–139 |
| 28 | 2 | 5-Cl | 3-$nC_4H_9$ | 4-Cl | H | $NH_2$ | 119–120 |
| 29 | 3 | 5-Cl | 3-$nC_4H_9$ | 4-Cl | H | ONa | 220–228 |
| 30 | 1 | 5-Cl | 3-$nC_4H_9$ | 4-Cl | H | ONa | 175–180 |
| 31 | 2 | 5-Cl | 3-$nC_4H_9$ | 4-$CH_3$ | H | $NH_2$ | 138.5–139.5 |
| 32 | 3 | 5-Cl | 3-$nC_4H_9$ | 4-$CH_3$ | H | $NH_2$ | 77–78 |
| 33 | 3 | 5-Cl | 3-$nC_4H_9$ | 4-Cl | H | $NH_2$ | 106.5–107.5 |
| 34 | 2 | 5-Cl | 3-$CH_3$ | 4-Cl | H | $N(C_2H_5)_2$ | 142–143 |
| 35 | 3 | 5-Cl | 3-$CH_3$ | 4-Cl | H | $N(C_2H_5)_2$ | 122–123 |
| 36 | 3 | 5-Cl | 3-$CH_3$ | 4-Cl | H | OMg/2 | >230 |
| 37 | 3 | 5-Cl | 3-$CH_3$ | 4-Cl | H | pyrrolidinyl | 130–131 |
| 38 | 2 | 5-Cl | 3-$CH_3$ | 4-Cl | H | pyrrolidinyl | 165–166 |
| 39 | 2 | 5-Cl | 3-$CH_3$ | 4-Cl | H | piperidinyl | 155–156 |

The compounds of the invention were subjected to pharmacological tests and these showed their activity on the central nervous system.

The acute toxicity was determined by intraperitoneal administration to mice. The $LD_{50}$ (50% lethal dose), which causes the death of 50% of the animals, ranges from 250 to >1000 mg/kg animal body weight.

The antidepressive activity of the compounds was shown by the antagonism towards the head twitches caused by L-5-hydroxytryptophan in mice.

The mice (male CD1, Charles River France, 18–22 g body weight) received increasing doses of the products to be studied, or the solvent, simultaneously with a 250 mg/kg animal body weight dose of L-5-HTP, administered subcutaneously. Forty-five minutes after this injection of L-5-HTP, the number of head twitches for each mouse is counted for one minute.

The average number of head twitches and also the percentage variation relative to the control batch are calculated for each treatment.

Using the effect-dose curve, the $AD_{50}$ (50% active dose or the dose which reduces the average number of head twitches by 50%) is determined by the graphical method of Miller and Tainter, Proc. Soc. Exp. Biol. Med. (1944), 57–261.

The $AD_{50}$ of the compounds of the invention varies from 40 to 60 mg/kg animal body weight, administered intraperitoneally.

The anticonvulsant activity of the compounds was shown by the antagonism towards the mortality caused by bicuculline in mice.

Bicuculline is a relatively selective blocker of post-synaptic GABA-ergic receptors and its convulsant and lethal effects are antagonised by compounds which increase the level of GABA in the brain or which possess a GABA-mimetic activity, "GABA" is an abbreviation for γ-amino-butyric acid.

The 50% active dose ($AD_{50}$) of the substances studied, that is to say the dose which protects 50% of the animals against the effect of bicuculline, were evaluated.

The $AD_{50}$ of the compounds of the invention varies from 10 to 100 mg/kg animal body weight, administered intraperitoneally.

The compounds of the invention are active as antidepressants and anticonvulsants and also possess anxiolytic, analgesic, anti-inflammatory, ulcer-inhibiting, gastric antisecretory and antihypertensive properties. They can be used in human and veterinary therapy for the treatment of various diseases of the central nervous system, for example for the treatment of depressions, psychoses and certain neurological diseases such as epilepsy, spasticity and dyskinesia, and for the treatment of gastric and duodenal ulcers.

The compounds of the invention are also active in the cardiovascular field and can therefore be used for the treatment of various diseases in this field.

The invention consequently includes all pharmaceutical compositions which contain as active ingredient, compounds of general formula (I) in association with any excipients suitable for their administration, in particular their oral administration (tablets, coated tablets, gelatin capsules, ordinary capsules, cachets, solutions or suspensions to be taken orally) or parenteral administration.

The daily dosage can range from 100 to 3000 mg.

I claim:

1. A benzylidene derivative of the formula:

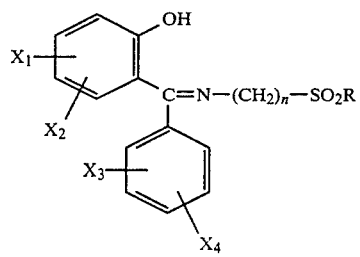

wherein n represents an integer from 1 through 4, R represents an amino radical, a monoalkylamino group containing 1 through 4 carbon atoms in the alkyl radical, a dialkylamino group containing 1 through 4 carbon atoms in each alkyl radical, or when n represents 2, 3 or 4 a group $$-N \quad (CH_2)_m$$

in which m represents 4 or 5, or a group —OM in which M represents an alkali metal or alkaline earth metal, and $X_1$, $X_2$, $X_3$ and $X_4$ each represent, independently of one another, a hydrogen atom, a halogen atom, or an alkyl radical of 1 through 6 carbon atoms.

2. A benzylidene derivative according to claim 1 of the formula:

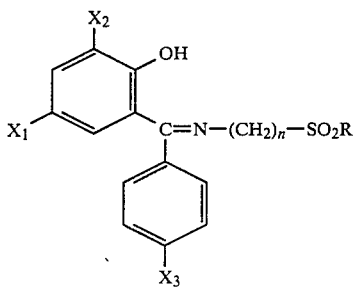

wherein n, R, $X_1$, $X_2$ and $X_3$ are as defined in claim 1.

3. A benzylidene derivative according to claim 2 wherein n represents 2 or 3, R represents the amino radical or a diethylamino group, or a group —ONa, —OCa/2 or —OMg/2, $X_1$ represents a halogen atom or the methyl radical, $X_2$ represents a hydrogen atom or an alkyl radical of 1 through 6 carbon atoms, and $X_3$ represents a halogen atom or the methyl radical.

4. A benzylidene derivative according to claim 1 wherein the halogen atom is chlorine.

5. A benzylidene derivative according to claim 1 which is 3-[(5-chloro-2-hydroxy-3-methylphenyl)(4-chlorophenyl)methylene]-aminopropanesulphonamide.

6. A benzylidene derivative according to claim 1 which is 2-[(5-chloro-2-hydroxy-3-methylphenyl)(4-chlorophenyl)methylene]-aminoethanesulphonamide.

7. A pharmaceutical composition which comprises, as active ingredient, a benzylidene derivative as claimed in claim 1 in association with a sufficient amount of a pharmaceutically-acceptable excipient.

* * * * *